United States Patent [19]

Romera-Sierra et al.

[11] 4,207,689

[45] Jun. 17, 1980

[54] PRESERVATION OF ANIMAL SPECIMENS

[75] Inventors: Cesar Romera-Sierra, Bath; John C. Webb, Kingston, both of Canada

[73] Assignee: Queen's University at Kingston, Kingston, Canada

[21] Appl. No.: 929,748

[22] Filed: Jul. 31, 1978

[30] Foreign Application Priority Data

Aug. 5, 1977 [CA] Canada .................................. 284215

[51] Int. Cl.² ............................................. G09B 23/36
[52] U.S. Cl. ..................................................... 35/20
[58] Field of Search .................... 35/20; 428/16; 27/21

[56] References Cited

U.S. PATENT DOCUMENTS

| | | | |
|---|---|---|---|
| 3,573,082 | 3/1971 | Fremling | 428/16 |
| 3,780,452 | 12/1973 | Jackson | 35/20 |

FOREIGN PATENT DOCUMENTS

| | | | |
|---|---|---|---|
| 547105 | 5/1956 | Belgium | 35/20 |
| 450350 | 7/1936 | United Kingdom | 35/20 |

OTHER PUBLICATIONS

Jack McClintock, "Freeze–Drying and Museums", Washington Post, Jul. 26, 1971.

*Primary Examiner*—Harland S. Skogquist
*Attorney, Agent, or Firm*—Richard J. Hicks; Stanley E. Johnson

[57] ABSTRACT

A method for preparing a naturally colored and flexible freeze dried animal specimen for study or display purposes, in which a lubricating agent is injected into the major joints and the specimen is wrapped in a moistened cheese cloth prior to freezing and drying. After freeze drying the specimen is soaked in an organic solvent to remove substantially all of the lipids from adipose tissue and bone marrow therein and then softened and manipulated to restore substantially natural movement thereto. A polymerizable silicone rubber may be rubbed into the dried and softened tissue to replace lost bulk and to seal the tissue against reabsorption of water, so that the dried specimen can be stored indefinitely in an open atmosphere.

16 Claims, No Drawings

PRESERVATION OF ANIMAL SPECIMENS

This invention relates to the preservation of biological specimens, and more particularly to the preservation of animal specimens by freeze drying for demonstration and teaching purposes.

Heretofore it has been accepted practise to preserve and store biological specimens such as gross anatomical specimens and entire dead bodies, both animal and human, in a preservation solution of formaldehyde or other equivalent substance contained in a suitable specimen or museum jar. Such preservation is not, however, without disadvantages such as the fact that such specimens tend to lose their natural colour, they tend to shrink considerably from their natural size, stiffen and distort considerably thus becoming unnatural in appearance and difficult to handle. Many people find formaldehyde objectionable to work with not only because of its smell but also because it can cause irritation of the skin, nose and eyes.

Alternative methods for preserving biological specimens and in particular animal specimens have, therefore, been the subject of considerable study. As used herein, the term "animal specimen" is intended to cover specimens of all forms of animal life, human and nonhuman, birds, mammals, fish, insects, crustaceans and other exoskeletons and the like, either whole or parts thereof. Theoretically, at least, whole animals such as whales or elephants could be treated according to the techniques described herein although as a practical matter it is probably better to dissect such large animals before treatment. Considerable attention has been focussed, primarily by taxidermists and museum curators, on freeze drying techniques for preserving animals, both whole and small specimens thereof, and such techniques are now considered standard for the preparation of rigid specimens for display in museums and the like. Freeze drying depends upon the cryogenic removal of water from tissues. As water is the essential medium for the bacterial, fungal and autodigestive enzymes that cause the deterioration of biological matter, its absence prevents the decay of tissues. Water is removed most efficiently, and with a minimum of damage and distortion to tissues by freeze dry techniques, i.e. by freezing the water and sublimating it off under vacuum. Specimens lose between 45 and 55% of their weight due to water loss but, if done correctly, the shrinkage of tissues and tissue space can be controlled. Detailed descriptions of the techniques employed can be found in the literature and attention is particularly directed to Ann. Mag. Nat. Hist. (London) 13/7 (1964) Harris R. H. "Vacuum Dehydration and Freeze Drying of Entire Bilogical Specimens" and to "Curator" III/1 (1960) Meryman H. T. "The Preparation of Biological Museum Specimens by Freeze Drying". In these techniques animal specimens as large as 6 foot alligators have been desanguinated, eviscerated, posed in the desired final position by freezing and then freeze dried at temperatures of the order of $-10°$ C. or lower and at pressures of the order of 1 micron of mercury. Specimens prepared in this way can be displayed in room atmosphere without benefit of air conditioning or humidity control for at least several years without visible degradation or decay. Surprisingly, such disiccated specimens are not hydroscopic and do not absorb appreciable moisture from the air. Such specimens are not, however, impervious to parasites, nor are they inedible (at least by rodents). Further, although freeze drying removes some 95% of the water in the specimen, the lipid or fat content in adipose tissue and bone marrow is not affected and may, in time, decay. Such freeze dried specimens are, of course, entirely rigid and may be somewhat shrunken and hence quite unsuitable for anatomical studies, dissection and the like. Further, because no attempt has heretofore been made to properly treat and preserve the interior of the larger bones, which contain considerable bone marrow, handling of such bones during anatomical or other studies may constitute a serious health hazard. Bone marrow is known to be a prime source of infection and disease and many microorganisms, viruses and the like are totally unaffected by deep freezing and drying and can therefore remain dormant for years.

It is an object of the present invention to provide a method for preparing freeze dried biological specimens, and particularly animal specimens as hereinbefore defined, which can be stored under ambient conditions for extended periods of time without degradation and which are substantially odour free, naturally coloured and possess substantially natural flexibility.

Another object of the invention is to provide a substantially odour-free, naturally coloured and flexible freeze dried animal specimen which is suitable for anatomical or other studies without risk of infection or other contamination.

Thus by one aspect of this invention there is provided in a method for preparing freeze dried biological specimens in which a posed specimen is freeze dried at a temperature below about $-10°$ C. and a pressure below about 0.10 torr, the improvement for preparing a substantially naturaly coloured and flexible animal specimen comprising:

(a) injecting a lubricating agent into and manipulating at least selected joints in said specimen prior to freeze drying;

(b) soaking the freeze dried specimen in an organic solvent so as to remove substantially all lipids from adipose tissue and bone marrow therein; and (c) applying a softening agent to and manipulating tissues of said freeze dried specimen.

By another aspect of this invention there is provided a freeze dried animal specimen characterized by substantially natural flexibility and coloration and freedom from odour.

The precise procedure to be carried out in the preparation of flexible freeze dried animal specimens depends, in large part, upon the particular specimen under consideration and the final end use for which it is intended. Clearly, large specimens, such as whole human cadavers and large animals such as bears, elephants and the like require more preparation than small animals or small parts thereof. Insects and the like require the least preparation simply because their structure is much less complicated.

(i) Preparation for Freeze Drying

As previously noted, although whole large cadavers may be freeze dried, the time for so doing is of the order of months or years, and is consequently not generally practical due to space limitations in available freeze drying equipment. It is therefore, more usual to dissect the cadaver into a number of major sections of more suitable size for freeze drying in reasonable time. Generally, however, the first stage in the preparation is the flushing of the vascular system in the conventional manner for any embalming process—cutdowns are performed and cannulae inserted into both the common carotid and femoral arteries, and one jugular vein. The vascular system is then completely drained of blood and flushed at a suitable pulsating pressure, of the order of 1-10 lbs. using a peristaltic pump, with a suitable and conventional flushing solution, such as EPIC ® sold by The Embalmers Supply Co., Rexdale, Ont.

After the vascular system has been cleared, one of two routes may be followed. If the vascular tree is judged to be intact, i.e. there is no severe bloating, hemorrhage or extravascular accumulations of fluids, the vessels can be injected with a polymerizable silicone rubber injection compound such as MICROFIL ® sold by Canton Bio-Medical Products, Inc., Boulder, Colo. However, as such injection compounds penetrate to the level of the capillary bed, it is essential to ascertain the condition of the vascular bed before proceeding in order to determine the density of the product selected for injection into the vessels. In the likely event that the vascular tree is not intact relatively viscous red rubber latex should be injected into the arterial system and blue rubber latex into the venous system to facilitate good visualization of the vessels in the final product.

After gelling of the silicone or latex, the next step is to disarticulate and section the cadaver, as necessary, into manageable specimens that will fit into the freeze drying equipment, depending upon the kind of prepared specimen required. For example, some lower limb specimens may be sectioned through the sacrum and pubis, so as to show the origin of nerves to the lower limbs, attachment of genitals etc. Other specimens may be disarticulated at the head of the femur so that the pelvis and abdominal wall can be kept as an intact specimen. It is also desirable, at this stage, to remove all major viscera from thorax, abdomen and pelvis and to prepare them separately. Similarly the skull can be trepanned so that the brain can be removed and prepared separately to provide whatever finished specimen is desired such as a specimen of the meninges, ventricles or the brain itself. Preparation of the viscera, brain, etc. can be by any conventional method, including freeze drying and preferably the specimens are prepared in such a way that they can be reinserted into the finished specimens of the head, thorax and abdomen. Immediately upon removal, the viscera should be immersed in a hypertonic solution, such as a meat packing solution, in order to preserve as much of the original coloration as possible. Any suitable meat packing solution can be employed such as an aqeuous solution comprising $Na_2HPO_4$, $NaH_2PO_4H_2O$, ascorbic acid, NaCl, $NaNO_3$ and $NaNO_2$.

(ii) Skinning and Dissection

The next stage is generally to skin and dissect the specimen. Skinning facilitates the freeze drying of the underlying tissues but in those cases where it is desired to retain the skin on the specimen a series of perforations should be made so as to allow for the dehydration with minimal tissue destruction. Skinning is effected by known techniques. Care should be taken that neither the skin nor the underlying muscles, nerves or vessels are damaged. This is best achieved by blunt dissection. It is convenient to remove as much of the subcutaneous fat and fascia as possible with the skin. The dissection performed at this stage is solely for the purpose of maximizing the surface area/volume ratio. Therefore little cleaning of the tissues or fine dissection of smaller structures is normally done at this point. Time is generally of the essence as the as yet unpreserved specimen is usually undergoing some autolysis by this time. During the dissection, however, it is necessary to massage the muscles parallel to the fibres thereof and to manipulate the joints frequently. After the dissection has been completed, the major joint spaces are injected with a lubricant, such as glycerin or a silicone, and manipulated extensively so as to distribute it to all recesses of the space.

(iii) Posing

The posing of the specimen is the next important stage as it largely determines the ultimate shape of the specimen and, to some extent, the time required for freeze drying. Preferably, but not essentially, the posing is effected by wrapping the specimen with cloth or gauze strips. Cheesecloth is particularly suitable for this purpose. Preferably all structures are separated by at least two layers of cloth and, where possible, larger muscles are individually wrapped. The wrapped specimen is then shaped manually, in situ, so that the correct shape and relations are preserved. Cloth wrapping is particularly effective to support specimen structures and to prevent undue pressure thereon during the freeze-drying. The cloth also helps to prevent localized drying or "freezer-burn" of the skin. Preferably, but again not essentially, the wrapping cloths are soaked in a meat packing solution, such as that described hereinabove, in order to preserve natural colouring. It may be desirable to soak the entire wrapped specimen in a bath of the meat packing solution for a few hours before proceeding to the next stage in the posing process, namely that of freezing. Final positioning of the specimen is best effected by freezing in a conventional deep freezer, at $-30°$ C. or lower, in the most appropriate position. For example, upper and lower limb specimens should be suspended by wrist and ankle respectively, and lower limb specimens should be semi-flexed at hip, knee and ankle joints. Spot freezing with liquid nitrogen may also be employed to effect posing by surface freezing. The use of liquid nitrogen for general freezing is not recommended as the intense cold can cause cracking of the specimen.

(iv) Freeze Drying Treatment

Once the specimens have been posed they are ready for freeze drying by now conventional techniques. Weighed specimens are placed in a freeze-drying chamber which can be maintained at a temperature of the order of $-30°$ C. to $-50°$ C. and at a pressure between 0.05-0.10 torr. The specimens are weighed at intervals of approximately 48 hours and the chamber is defrosted each time. After 2-3 weeks, depending upon the size, thickness and nature of the specimen, the weight stabilizes at about 45-55% of the original and the specimen can be considered completely dried.

(v) Post Drying Treatment

After drying the specimens are removed from the freezer unit and stripped of as much of the cloth wrapping as possible, without damaging any of the now brittle structures. A hole, up to about a quarter inch diameter depending upon the size of the specimen, is drilled into each end of the larger long bones and other bony structures rich in bone marrow and the specimen is totally immersed in an organic solvent bath for a period up to about 24 hours or even longer. Any suitable organic solvent for lipids may be employed such as chloroform, although great care must be taken with this somewhat hazardous reagent, or acetone which is the preferred solvent. After soaking, the remainder of the cloth is removed and the entire specimen is manipulated to improve flexibility of joints and muscles. The specimen is then air dried for 24 hours or more, until it no longer smells of the solvent. A lubricant solution, such as 25% glycerin in water, is then massaged gently into the tissues so that they become soft and flexible. The joints are also manipulated and, where necessary, injected with glycerin or other lubricant such as a silicone, so that the full range of movement is restored.

(vi) Final Treatment

Although there is very little visible shrinkage of tissue during freeze drying, it is clear that considerable bulk due to water loss has been caused and it is usually preferred to replace this bulk with a suitable bulking compound, such as a polymerizable silicon rubber injection compound. A particularly suitable bulking compound has been found to be a mixture of Microfil ® Clear, Microfil ® MV-132 (diluent) and MV curing agent, sold by Canton Bio-Medical Products Inc. of Boulder, Colo. In a preferred procedure, MV diluent coloured with a small quantity of red dye is massaged into the tissues to facilitate penetration and absorption of the subsequent clear Microfil and to give the tissues some colour. A mixture of Microfil Clear, diluent and curing agent as hereinabove described is then thoroughly massaged into the tissues. In an alternative procedure the aforesaid bulking agent may be introduced into the tissues of the specimen prior to freeze drying in which case a large bulky specimen, well defined in its anatomical components, is produced. Important structures may be separated with small plastic chips so that the silicone rubber gels evenly over their surfaces and so that they can be clearly distinguished in the final product. After curing, excess gel is removed by rubbing gently, in a direction parallel to muscle or nerve fibres, with a gauze or cloth, and the preserving process is complete. Preserved specimens can be stored in the open air substantially indefinitely. Preferably, fine dissection is done when the preservation is complete, i.e. when the tissue is completely sealed and in no danger of reabsorbing water and deteriorating. Fine dissection can, however, be done at any time after the organic solvent treatment. Fine dissection consists generally of the removal of fascia, separation of finer structures and visualizing the deeper structures, i.e. the deep posterior compartment of the human leg is better visualized by sectioning soleus, plantaris, and the two heads of gastrocnemius just distal to their origins.

To further illustrate the present invention, but without limitation of the scope thereof, reference will be made to a typical procedure by way of example.

EXAMPLE 1

Preparation of a Cat for Biological Studies by Freeze Drying

A cat was killed by an overdose of Nembutal (250 mg/kg body weight), administered intra-peritoneally in order to keep the cat in a state of sleep for some minutes first. While the cat was still alive and its blood was circulating, it was given an intravenous perfusion of anticoagulant (heparin) and vasodilator (histamine). A second injection of Nembutal ensured death by cardiac arrest. The cat was then exsanguinated through the left femoral artery of the lingual vein. The blood was flushed out from the cat's body using a flushing solution comprising 1 oz/quart of water of EPIC ® drainage chemical (sold by Embalmers Supply Corporation, Rexdale, Ont.) at 2 lbs. pulsating pressure. Red latex was then injected into the arterial system and blue latex into the venous system to enhance visualization of the vessels in the final product. The latex was dissolved in equal parts with 2.5 m potassium acetate, injected into the specimen from a compressor-cannister at 2 lbs. pressure, and gelled at room temperature in about 4 hours. Similar latex injections were effected to emphasize the lymphatic, renal and hepatic systems.

The animal was then eviscerated through a midsagittal ventral incision into the thoracic and abdominal cavities. The viscera were extracted and placed in a jar of a meat packing solution comprising (gms/1. of water) 0.91 g. $Na_2HPO_4$, 2.42 g. $NaH_2PO_4 H_2O$, 1.5 g. ascorbic acid, 7.5 g. NaCl, 0.17 g. $NaNO_3$ and 0.11 g. $NaNO_2$ and kept for a maximum of 4 hours at 10° C., once the gastric and intestinal contents had been flushed out through a number of small incisions. The viscera were then prepared similarly to the remainder of the specimen. The major structures of the right limbs were then dissected and the overlying skin removed. The skin over the upper portions of the left side extremities was perforated to allow for the dehydration of these regions with minimal tissue destruction. The skull was trepanned for similar reasons. The major joints were then injected with 2 cc glycerin and manipulated for maximum flexibility. Individual structures and then the entire specimen were then wrapped in two layers of cheesecloth so as to maintain the structures in the entire specimen in as natural a position, relative to each other, as possible. The cheesecloth was moistened with the meat packing solution described above, to preserve the colour of the specimen. The wrapped specimen was then placed in a freeze drying chamber at −30° C. and 0.05 torr for approximately 3 weeks. The specimen was weighed every second day until the weight stabilized and the specimen judged to be fully dehydrated. As much of the wrapping cloth as possible without damaging any of the now brittle structures was removed and small holes were drilled in both ends of the long bones of the extremities. The specimen was then immersed in an acetone bath for 4–8 hours. Following the acetone treatment, which removed fat and bone marrow, the specimen was dried in a special fume container for 4 hours to remove all acetone. After drying, the specimen was placed in a 25% solution of glycerin in warm water and after 1–2 hours was gently massaged to increase penetration of the solution into the tissues, to increase softness and flexibility, until a thin coating of glycerin was left on the tissue surfaces and the brittleness gone. The joints were manipulated and the remainder of the cloth removed.

A mixture of MICROFIL ® clear with MV 132 (diluent) and curing agent was then rubbed into the tissues, which were separated with plastic chips as necessary to prevent sticking, and cured for 24 hours. Excess gelled Microfil was then removed by rubbing with cheesecloth in the direction of the fibrous structures until the gloss gave way to a natural appearance.

Finally, the treated viscera were replaced in the thoracic and abdominal cavities and sutured into place to allow study in their correct positions. The fur was then groomed with an ordinary hair conditioner. The cat was then stored in the open air and handled freely by anatomy students over a period of several years without visible deterioration or detectable odour.

EXAMPLE 2

Preservation of a Perch

After perfusion with latex as in Example 1 a ventral-dorsal incision was made thus splitting the fish in half with the bones, fins (except for one pectoral fin) and the viscera left intact and attached to one half, and only cutaneous and muscle tissue on the other. The cutaneous and muscle half was treated using a freeze-substitution technique in an alcohol solution. The other half was prepared by the same wrapping and freeze drying technique described in Example 1 with reference to a cat. After drying the two halves were fitted back together and finished with a silicon rubber (Microfil ®) treatment as described in Example 1.

We claim:

1. In a method for preparing freeze dried biological specimens in which a posed specimen is freeze dried at a temperature below about −10° C. and a pressure below about 0.10 torr, the improvement for preparing a substantially naturally coloured and flexible animal specimen comprising:
   (a) injecting a lubricating agent into and manipulating at least selected joints in said specimen prior to freeze drying;
   (b) soaking the freeze dried specimen in an organic solvent so as to remove substantially all lipids from adipose tissue and bone marrow therein; and
   (c) applying a softening agent to and manipulating tissues of said freeze dried specimen.

2. A method as claimed in claim 1 including introducing a polymerizable bulking agent into said softened tissues.

3. A method as claimed in claim 2 including injecting a polymerizable bulking agent into the vascular system of said specimen prior to freeze drying.

4. A method as claimed in claim 1, 2 or 3 wherein said animal specimen is posed prior to freeze drying by at least one (a) wrapping in cloth and (b) freezing, in a preselected position.

5. A method as claimed in claim 1, 2 or 3 wherein said animal is desanguinated prior to freeze drying.

6. A method as claimed in claim 1, 2 or 3 wherein said lubricating agent is selected from the group comprising a silicone oil and glycerine.

7. A method as claimed in claim 1, 2 or 3 wherein said organic solvent is selected from the group consisting of chloroform and acetone.

8. A method as claimed in claim 1, 2 or 3 wherein said softening agent is glycerine.

9. A method as claimed in claim 2 or 3 wherein said polymerizable bulking agent is selected from the group comprising rubber latex and silicone rubber.

10. A method as claimed in claim 1, wherein posing of said animal specimen is effected by cloth wrapping and treating with a hyper-tonic bacteriostatic and fixative solution.

11. A method as claimed in claim 10 wherein said bacteriostatic solution is a meat packing solution.

12. A method as claimed in claim 1, 2 or 3 including piercing at least one end of selected bones in said freeze dried specimen to thereby facilitate removal of lipids therefrom in step (b).

13. A method as claimed in claim 10 including freezing said cloth wrapped and treated specimen.

14. A method as claimed in claim 1 including introducing a bulking agent into tissues of said specimen prior to freeze drying.

15. A freeze dried, preserved animal specimen having a lubricating agent injected into the joints thereof and a polymerized bulking agent contained in the tissues thereof so as to provide an odour-free specimen having substantially permanent natural flexibility and coloration.

16. A freeze dried animal specimen as claimed in claim 15 wherein substantially all lipids and bone marrow in at least the larger bones thereof have been removed.

* * * * *